United States Patent [19]
Narbonne

[11] Patent Number: 5,545,802
[45] Date of Patent: Aug. 13, 1996

[54] APPARATUS AND PROCESS FOR TREATING MEDICAL FLUID WASTE CONTAINERS

[76] Inventor: Yves Narbonne, 6454 Beaucourt Street, Montreal-North Province of Quebec, Canada, H1G 2G4

[21] Appl. No.: 428,078

[22] PCT Filed: Aug. 27, 1993

[86] PCT No.: PCT/CA93/00351

§ 371 Date: Apr. 28, 1995

§ 102(e) Date: Apr. 28, 1995

[87] PCT Pub. No.: WO94/09830

PCT Pub. Date: May 11, 1994

[30] Foreign Application Priority Data

Oct. 30, 1992 [GB] United Kingdom ............. 9222777

[51] Int. Cl.⁶ .................. A62D 3/00; A61L 2/18
[52] U.S. Cl. .............. 588/249; 422/28; 422/294; 422/302
[58] Field of Search .............. 588/249; 422/28, 422/294, 302

[56] References Cited

U.S. PATENT DOCUMENTS

| 4,289,438 | 9/1981 | Murer | 414/412 |
| 4,340,152 | 7/1982 | Ekholm, Jr. | 222/1 |
| 4,776,488 | 10/1988 | Gurzan | 222/81 |
| 5,178,841 | 1/1993 | Vokins et al. | 422/302 |
| 5,382,406 | 1/1995 | Kruger et al. | 422/28 |

FOREIGN PATENT DOCUMENTS

| 0410306 | 1/1991 | European Pat. Off. | |
| 197809 | 9/1978 | France | 422/302 |

*Primary Examiner*—Ramon S. Britts
*Assistant Examiner*—Tara L. Mayo
*Attorney, Agent, or Firm*—Lowe, Price, LeBlanc & Becker

[57] ABSTRACT

The invention relates to an apparatus and method of treating a container holding a contaminated substance. The invention includes puncturing the container at different positions to allow the introduction of a disenfecting agent and a drainage of the contents of the container.

8 Claims, 4 Drawing Sheets

APPARATUS AND PROCESS FOR TREATING MEDICAL FLUID WASTE CONTAINERS

FIELD OF THE INVENTION

The present invention relates to an apparatus and a process for treating medical fluid waste bags. More particularly, the invention relates to an apparatus and a process for safely emptying and disinfecting medical fluid waste containers so that the medical fluid and the used containers can be safely disposed of separately.

BACKGROUND OF THE INVENTION

In hospitals, waste body fluids are drained from patients both during operations and during recovery from operations. For proper hygiene, the waste blood or body secretions are pumped into special medical fluid waste bags. Sterilization of the medical fluid waste bags before disposal has been known to be a difficult procedure.

In the art of waste disposal for waste contained in bags, it is known to provide a machine for mechanically opening and emptying bags containing a toxic product in which a conveyor automatically feeds the bags to severing means for cutting open the bags at which point the bags are automatically emptied thus separating the contents of the bag from the bag itself. Such a device is known from U.S. Pat. No. 4,289,438. In the medical field, it is known from U.S. Pat. No. 4,340,152 to provide a machine for the automatic emptying of bags containing frozen fresh blood and separating the bag from its contents. It is also known in the art from U.S. Pat. No. 4,776,488 to dispense a flowable material through a flexible wall of a bag in which a sealing ring is included in the bag by puncturing the bag using a tubular cutting member sealingly engaged to the bag and over the ring.

It is therefore an object of the present invention to provide an apparatus and a process for treating a bag containing medical fluid waste in which the bag, is safely emptied for safe disposal of its contents as liquid waste, in which the bag is properly disinfected for safe disposal or recycling of the bag.

SUMMARY OF THE INVENTION

According to the invention there is provided an apparatus for treating a container, such as a bag, containing a contaminated substance comprising a housing, means for holding the bag and means for severing the container to allow contents of the bag to empty, in which the apparatus is characterized in that the container is a medical fluid waste container, the housing has a sealable closure, the means for holding at least one medical fluid waste container upright in the housing, tile means for severing comprise means for puncturing an upper portion of the container to produce an upper puncture hole through which a disinfecting agent can be injected and means for cutting a lower portion of the container to produce a lower hole through which tile agent can drain. The apparatus according to the invention further comprises means for injecting the agent into the upper puncture hole, and means for spraying an interior of tile housing, and an outside of the container with the disinfecting agent to prevent contamination of tile housing interior and the outside of the container.

The process according to the invention comprises steps of holding the medical fluid waste container upright in the sealed housing, puncturing an upper portion of the container to produce an upper puncture hole through which a disinfecting agent can be injected, cutting a lower portion of the container to produce a lower hole through which the disinfecting agent can drain, injecting the disinfecting agent into the upper puncture hole and spraying an interior of the housing and an outside of the container with the disinfecting agent to prevent contamination of the housing interior and the container outside.

To improve mixing of the contaminants in the container with the disinfecting agent, the upper puncture hole can be made first following which disinfecting agent is injected into the upper puncture hole to completely fill the container before the lower hole is cut by the cutting means causing the full container to rapidly drain. By completely filling the container from the top before cutting at the bottom, cutting of the container is improved.

BRIEF DESCRIPTION OF THE DRAWINGS

The invention will now be better understood by way of the following detailed description of a preferred embodiment with reference to the appended drawings in which.

DETAILED DESCRIPTION OF THE PREFERRED EMBODIMENT

Figure 1:
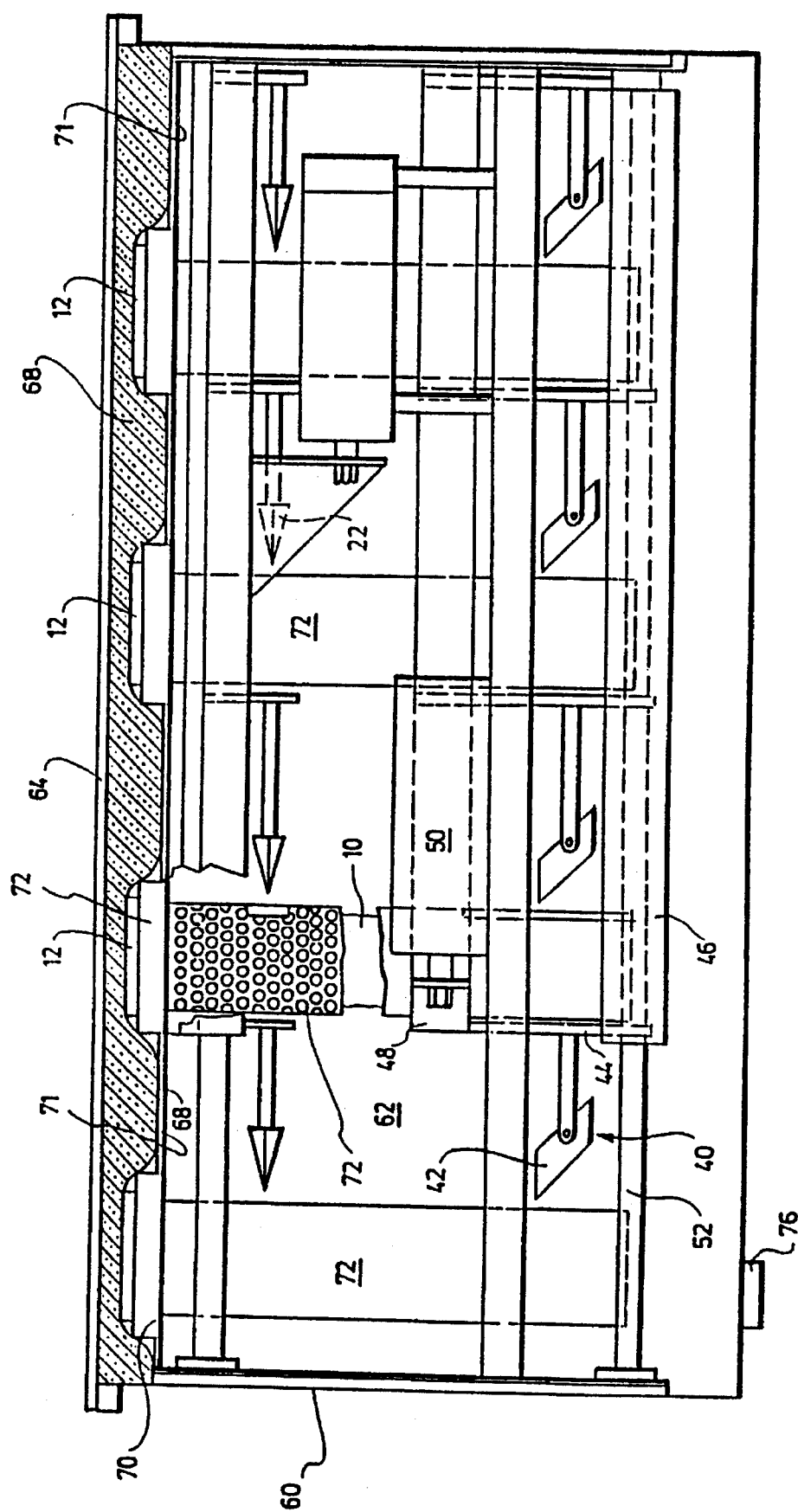
FIG. 1 is a side sectional view of the apparatus according to the preferred embodiment illustrating a series of puncturing means and cutting means in the initial position before engagement provided inside a housing.
Figure 2:
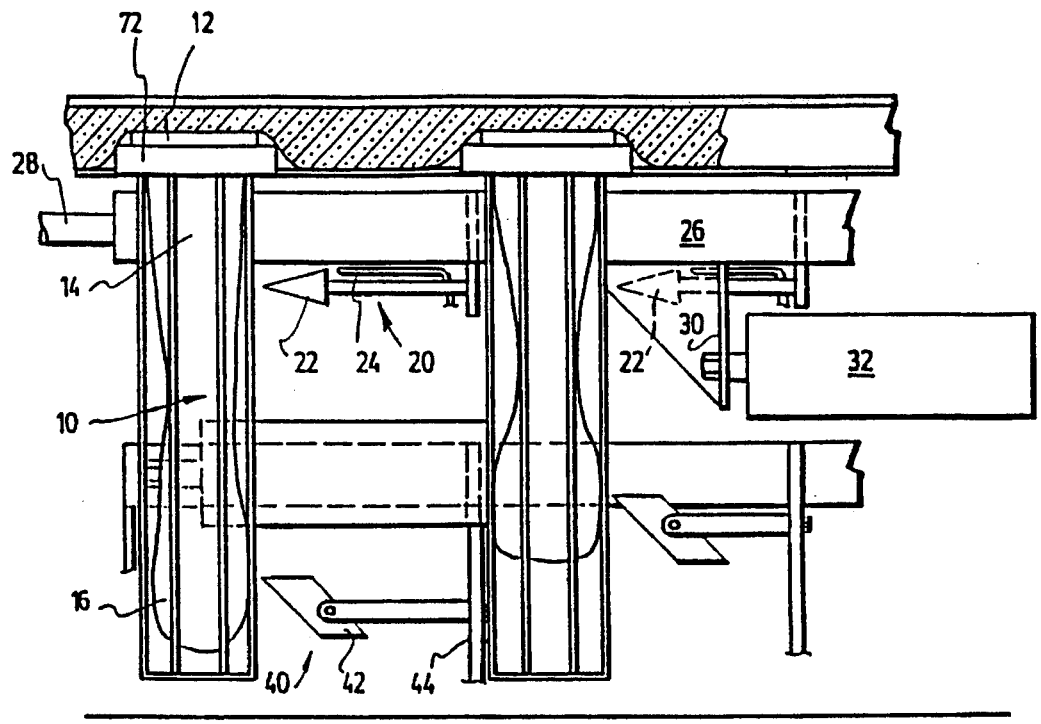
FIG. 2 is an enlarged partial view of FIG. 1, showing only two adjacent cutting and puncturing means.

As shown in FIGS. 1 and 2, a medical fluid waste bag (10) has an upper plastic lid (12) which is used for handling the bag and acting as a support when the bag is placed in a holder and receiving waste fluids from a patient such as blood or other fluids drained during or after an operation. Each bag (10) has an upper portion (14) and a lower portion (16) and the length of bag (10) as well as the diameter of its lid (12) will vary somewhat from one supplier to the next. As shown in FIG. 2, the fluid waste is largely contained in the lower portion (16) of bag (10) since bag (10) may be only about half full as shown.

Figure 3:
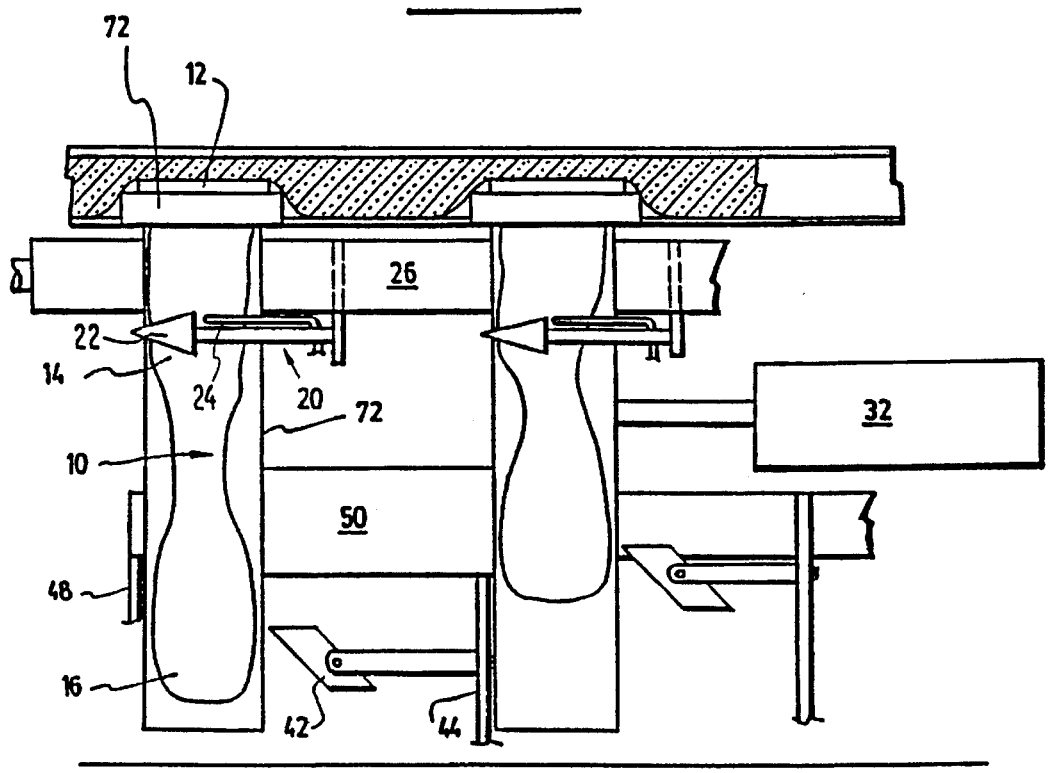
FIG. 3 is a view similar to FIG. 2 in which the bags have been punctured by the puncturing means and the injecting means have penetrated through the upper puncture hole.

With reference to FIGS. 2 and 3, there is shown puncturing means generally referenced by reference numeral (20) which include a puncturing tip (22) able to pierce the plastic wall material of bag (10). Tip (22) is mounted on an arm to a carriage (26) which supports a disinfecting agent spray nozzle (24) for each tip (22). Tip (22) is preferably flared and nozzle (24) is preferably within a cylindrical volume traced as the base of the tip (22) moves forward in order that nozzle

(24) easily enters bag (10) following tip (22). Carriage (26) slides on shaft (28) and is caused to move forward and backward under the action of a piston (32) connected to the carriage by a link rod (30). The apparatus of the present invention can process more than one bag (10) at a time, and in the preferred embodiment, eight bags (10) can be processed at a time, although more or less are possible. As shown in FIG. 3, pneumatic cylinder (32) is activated to advance tips (22) clear across upper portions (14) of bags (10) thus inserting nozzles (24) into the middle of upper portions (14). As shown in FIGS. 2 to 5, knives (42) are provided at different heights for cutting bottoms of bags (10) of different lengths. In practice, the apparatus may be set up to receive two or three different kinds of bags, with stations or cages (72) being set up with their knives (42) adjusted for specific kinds of bags. The cage (72) would be reserved for the specific kind of bag, until the knife (42) is readjusted. Each cage (72) includes an upper rim against which lids (12) are seated. The cages (72) are fastened into holes (70) in upper sheet (71) by a twist-lock connection which provides a watertight and air tight seal between the upper rim and sheet (71). Therefore, the same size holes (70) may conveniently be provided, while by changing cages (72) the diameter of the cage can be changed to receive bags (10) of different diameters, and lids (12) of correspondingly different diameters.

Figure 4:
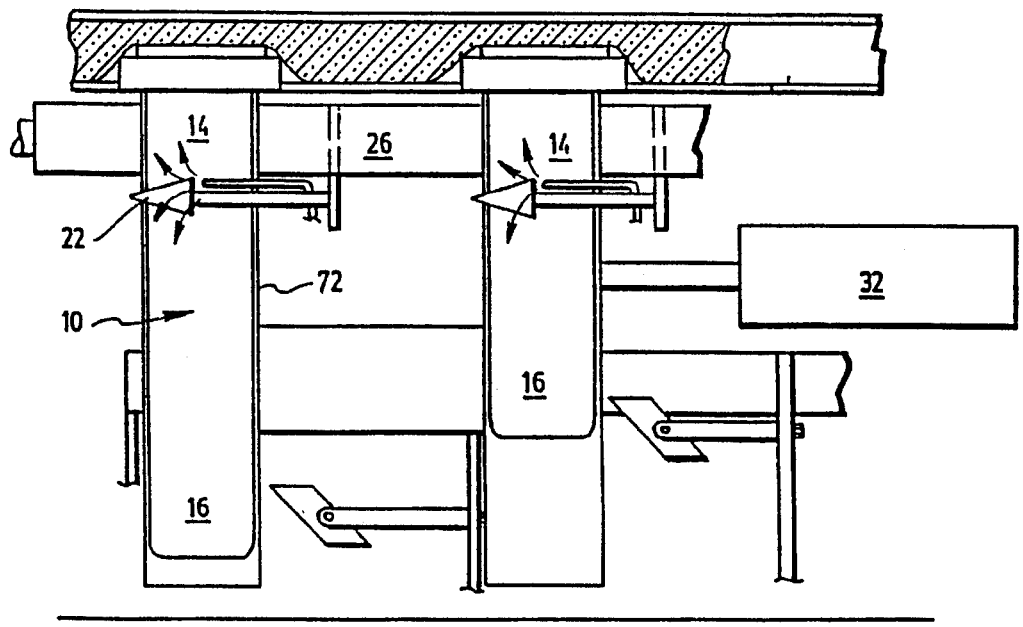
FIG. 4 is a view similar to FIG. 3 in which injection of disinfecting agent has begun to fill the waste bags with disinfecting agent.

Next, as shown in FIG. 4, nozzle (24) is supplied with water carrying a disinfecting agent under reasonably high pressure (good line pressure is sufficient) which causes bag (10) to fill up and the fluid waste to be mixed with the disinfecting agent.

Figure 5:
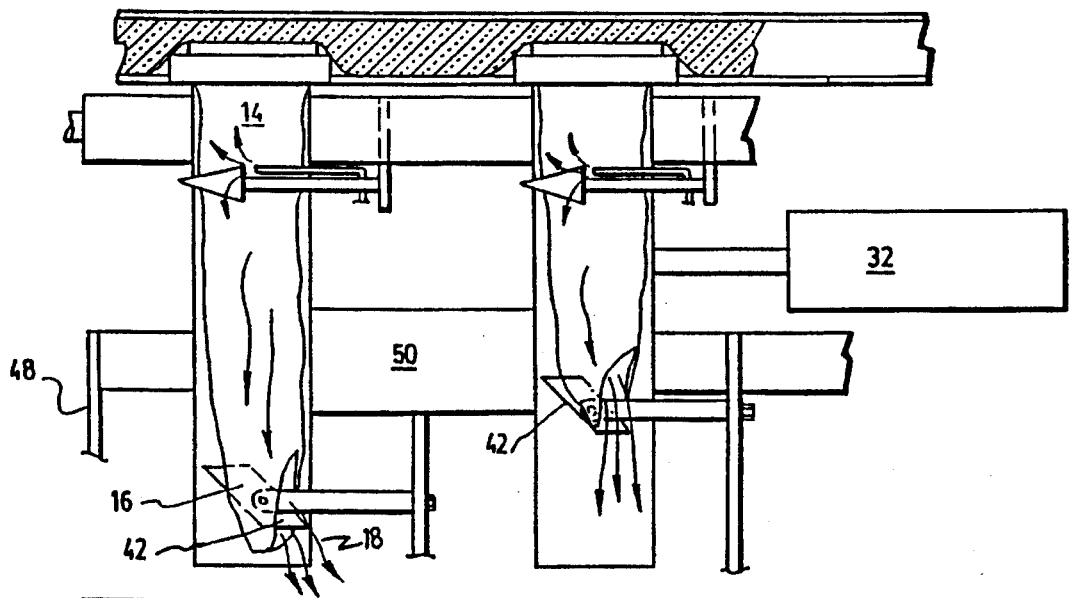
FIG. 5 is a view similar to FIG. 4 in which the cutting means have been advanced to cut a lower portion of the bags allowing the medical fluid waste and disinfecting agent contained therein to drain.

As shown in FIG. 1, cutting means (40) include a knife (42) mounted on a height adjustable bracket (44) which is in turn mounted to a carriage (46) displaceable along a shaft (52) under the action of piston (50) actuating link rod (48). When bag (10) is full as shown in FIG. 4, knife (42) is caused to advance as shown in FIG. 5 thus slicing open lower portion (16) of bag (10) allowing the mixture of fluid waste (18) and disinfecting agent to drain out through the bottom. By filling bag (10) first with disinfecting solution or agent, a certain fluid pressure at the lower portion of the bag develops and help give the bag some strength, making it easier for the knife (42) to cut the bag (10). Disinfecting agent may be supplied to nozzle (24) for an amount of time deemed sufficient to completely flush out and disinfect the inside of bag (10).

To ensure a complete and safe disinfecting of bag (10), the exterior of bag (10) is sprayed by jets (74) (see FIG. 6) similarly supplied with disinfecting agent contained in water under pressure. Of course, jets (74) also spray and disinfect all the components inside chamber (62) so that any biological waste is washed away and disinfected from all components of the apparatus so that the components can be serviced without danger of contamination.

Figure 6:
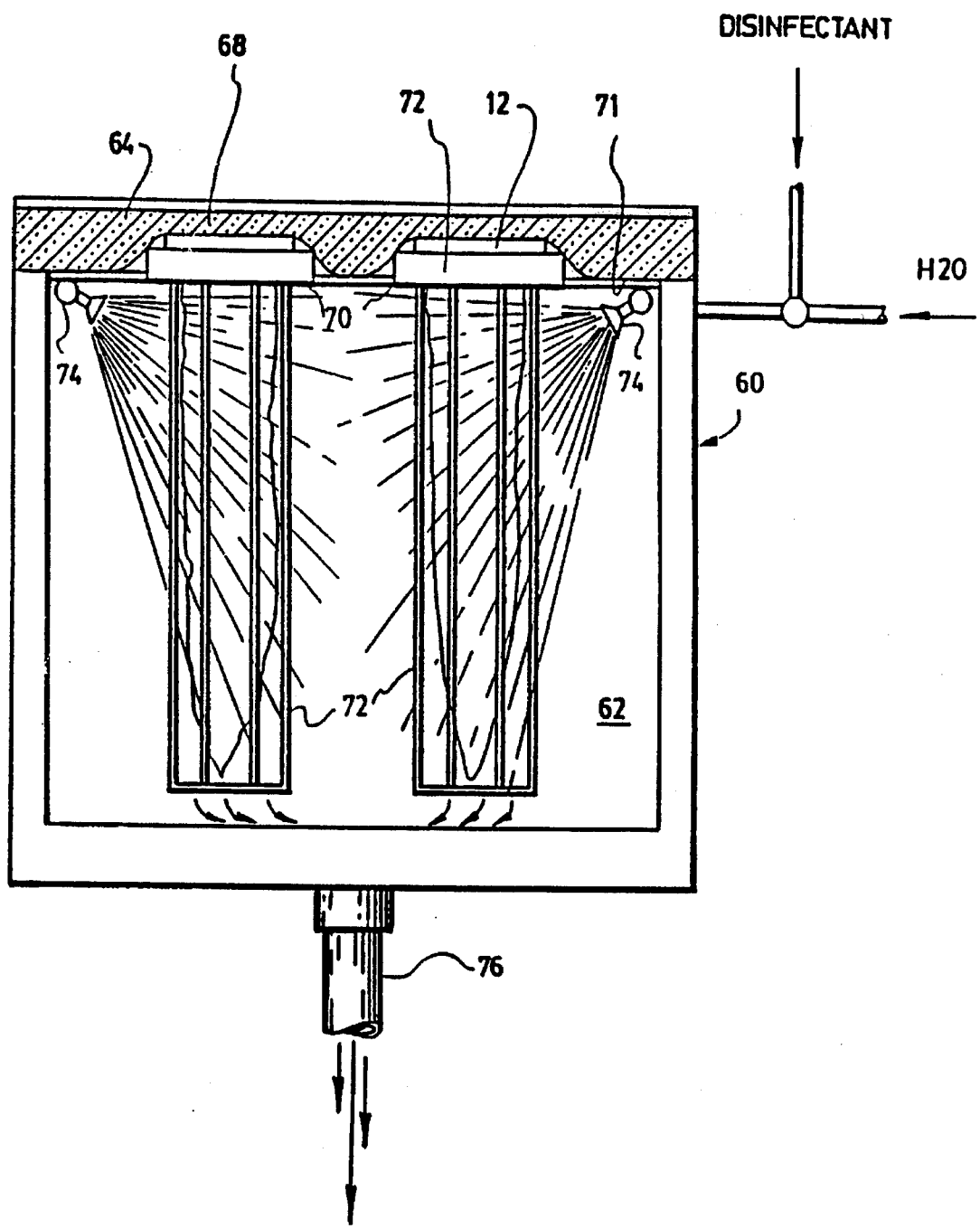
FIG. 6 is a partial cross-sectional end view of the apparatus according to the preferred embodiment illustrating the bags held by the holding means being sprayed by the spraying means with the puncturing means and cutting means not shown for clarity of illustration.

As shown in FIG. 6, the apparatus according to the preferred embodiment has a housing (60) including a chamber (62) having top sheet (71) including a plurality of holes (70) (only two are illustrated) which provide seating rims for cages (72) in which lids (12) make sealing contact as bags (10) are inserted into cages (72) located inside chamber (62). Cage (72) is shown in FIG. 1 to comprise a perforated cylinder, and in FIGS. 2 and 6 a cage with vertical bars. In the case of FIG. 1, the perforated cylinder is provided with openings for receiving tip (22) and knife (42), and in the case of the vertical bar cage, the spacing between bars is made wide enough where the tip (22) penetrates. A resilient pad (68) on the inside of cover (64) provides a means for securely holding lid (12) in hole (70) during the spraying and disinfecting process. If some of the plurality of holes (70) in housing (60) are not required during a disinfecting process, a disk-shaped plug is inserted into those holes (70) which are not to be used.

While the spray action of injection nozzle (24) provides thorough and vigorous cleansing and disinfecting of the inside of the bag, the spray jets (74) thoroughly clean the outside of bag (10) which is of course punctured in its upper portion and cut in its lower portion (16) during processing. Even though bag (10) is cut during treatment, it remains inside cage (72) and attached to lid (12). The disinfected medical fluid waste and the excess disinfecting agent collect at the bottom of chamber (62) flowing into drain (76). Of course, it is possible to subject the effluents to a further sterilization process such as heat treatment, UV irradiation or filtering before draining in the municipal sewer.

As shown in FIG. 6, the disinfectant can be automatically fed into the flow of water under line pressure using known backflow preventers, check valves and mixers.

As can be understood, the apparatus according to the present invention can be constructed to operate fully automatically with preprogrammed cycle times and movements of the puncturing and cutting means to provide error free secure sterilization of medical fluid waste bags on a regular basis for safe disposal of the medical fluid waste and thereafter of the disinfected medical fluid waste bags. Features such as a lock on cover (64) to prevent interruption of the disinfecting process once started as well as an automatic selection for different degrees of disinfecting are of course possible. As can be appreciated, the present invention safely washes out medical waste containers in a closed environment without exposing the operator to potentially biologically dangerous emissions which would be emitted if the containers were manually opened and washed out.

The bags (10) could be replaced by rigid containers of a similar shape. In this case, the puncturing means could comprise a drill (waterproof electric or pneumatic). The cage (72) would not be essential, and the container could be held in place by its lid or by other means such a clamp or guide. The cutting means could comprise a small rotary saw slicing open a thin hole in the bottom, or a drill making a hole in the bottom (moving vertically). It would even be possible to provide a rigid container with knock out tabs, one in upper portion (14) and another in the bottom (16), wherein the puncturing means would knock out the upper tab, and the cutting means would knock out the bottom tab. The disinfectant nozzle need not penetrate the container, but instead the water jet can be directed into the container through the knock out. In any event, the preferred method of washing remains the same, namely, the container is filled from the upper part until the container is full, then the lower part is opened, and the inside of the container is rinsed from the upper part down.

I claim:

1. Apparatus for treating a container containing a contaminated substance comprising a housing (60), means for holding the container, and means for severing the container to allow contents of the container to empty characterized in that:

said container is a medical fluid waste container;

said housing includes means (64,68) to seal said container in said housing;

said means for holding at least one said medical fluid waste container upright in said housing;

said means for severing comprise means for puncturing an upper portion of said at least one container thereby producing an upper puncture hole through which a disinfecting agent can be injected and means for cutting a lower portion of said at least one container thereby producing a lower hole through which both said agent and said medical fluid waste can drain; and in that the apparatus further comprises:

means for injecting said agent into said upper puncture hole; and means for spraying an interior of said housing and an outside of said at least one container with said agent to prevent contamination of said housing interior and said container outside.

2. Apparatus as claimed in claim 1, wherein said container is a bag comprising a rigid lid and a flexible cylindrical tube body, said housing includes an upper sheet provided with at least one opening including a rim on which said lid may rest, and said seal means comprise a cover having a resilient pad for pressing said lid against said rim to make sealing contact.

3. Apparatus as claimed in claim 2, wherein said holding means comprise a cage, whereby said bag is held by its lid at said opening and said body is confined by said cage, said cage including openings for allowing said severing means to pass through said cage.

4. Apparatus as claimed in claim 3, wherein said cage is a perforated cylindrical tube.

5. Apparatus as claimed in claim 1, wherein said cutting means comprise a knife mounted to a carriage by a height adjustable bracket.

6. Apparatus as claimed in claim 1, wherein said puncturing means comprise cone shaped tip mounted to a carriage, and said injecting means comprise a nozzle also mounted to said carriage such that an outlet of said nozzle follows behind a base of said cone into said container.

7. Process for treating a container containing a contaminated substance comprising the steps of holding the container in a housing, severing the container and allowing contents of the container to empty, characterized in that:

said container is a medical fluid waste container;

said step of holding comprises holding at least one medical fluid waste container upright in said housing, said housing being sealed;

said step of severing comprises puncturing an upper portion of said at least one container thereby producing an upper puncture hole through which a disinfecting agent can be injected, and cutting a lower portion of said at least one container thereby producing a lower hole through which both said agent and said medical fluid waste can drain;

and in that the process further comprises steps of:
injecting said agent into said upper puncture hole; and
spraying an interior of said housing and an outside of said at least one container with said agent to prevent contamination of said housing interior and said container outside.

8. Process as claimed in claim 7, wherein said step of cutting said lower portion is carried out sufficiently long after said step of injecting said agent into said upper puncture hole in order to fill said container before draining through said lower hole.

* * * * *